(12) United States Patent
McLaughlin et al.

(10) Patent No.: US 8,310,415 B2
(45) Date of Patent: Nov. 13, 2012

(54) MEDICAL DEVICES USING BISTABLE DISPLAYS

(75) Inventors: Brian McLaughlin, Media, PA (US); Ian M. Shipway, Bryn Mawr, PA (US); John Quinlan, Spring City, PA (US)

(73) Assignee: Animas Corporation, West Chester, PA (US)

( * ) Notice: Subject to any disclaimer, the term of this patent is extended or adjusted under 35 U.S.C. 154(b) by 529 days.

(21) Appl. No.: 12/570,003

(22) Filed: Sep. 30, 2009

(65) Prior Publication Data

US 2010/0079360 A1 Apr. 1, 2010

Related U.S. Application Data

(60) Provisional application No. 61/101,298, filed on Sep. 30, 2008.

(51) Int. Cl.
*G09G 3/30* (2006.01)

(52) U.S. Cl. .......................................... 345/76; 604/131
(58) Field of Classification Search .................... None
See application file for complete search history.

(56) References Cited

U.S. PATENT DOCUMENTS

| 7,335,405 B2 * | 2/2008 | Dubois et al. | 428/1.3 |
| 8,105,279 B2 * | 1/2012 | Mernoe et al. | 604/131 |

\* cited by examiner

*Primary Examiner* — Muhammad N Edun
(74) *Attorney, Agent, or Firm* — Wayne C. Jaeschke, Jr.

(57) ABSTRACT

The invention relates to a novel display system for a drug delivery device that reduces power consumption and permits the user of the device to see messages when the device is not in a powered state or when the device has encountered an error condition. By using a bistable display, the medical device is able to maintain messages that can been seen by the user even when the device's power supply is exhausted or when the device has encountered an error that interrupts its normal operation. The use of such a display also improves the battery life by eliminating the need to provide power to the display screen when it is not being updated.

2 Claims, 6 Drawing Sheets

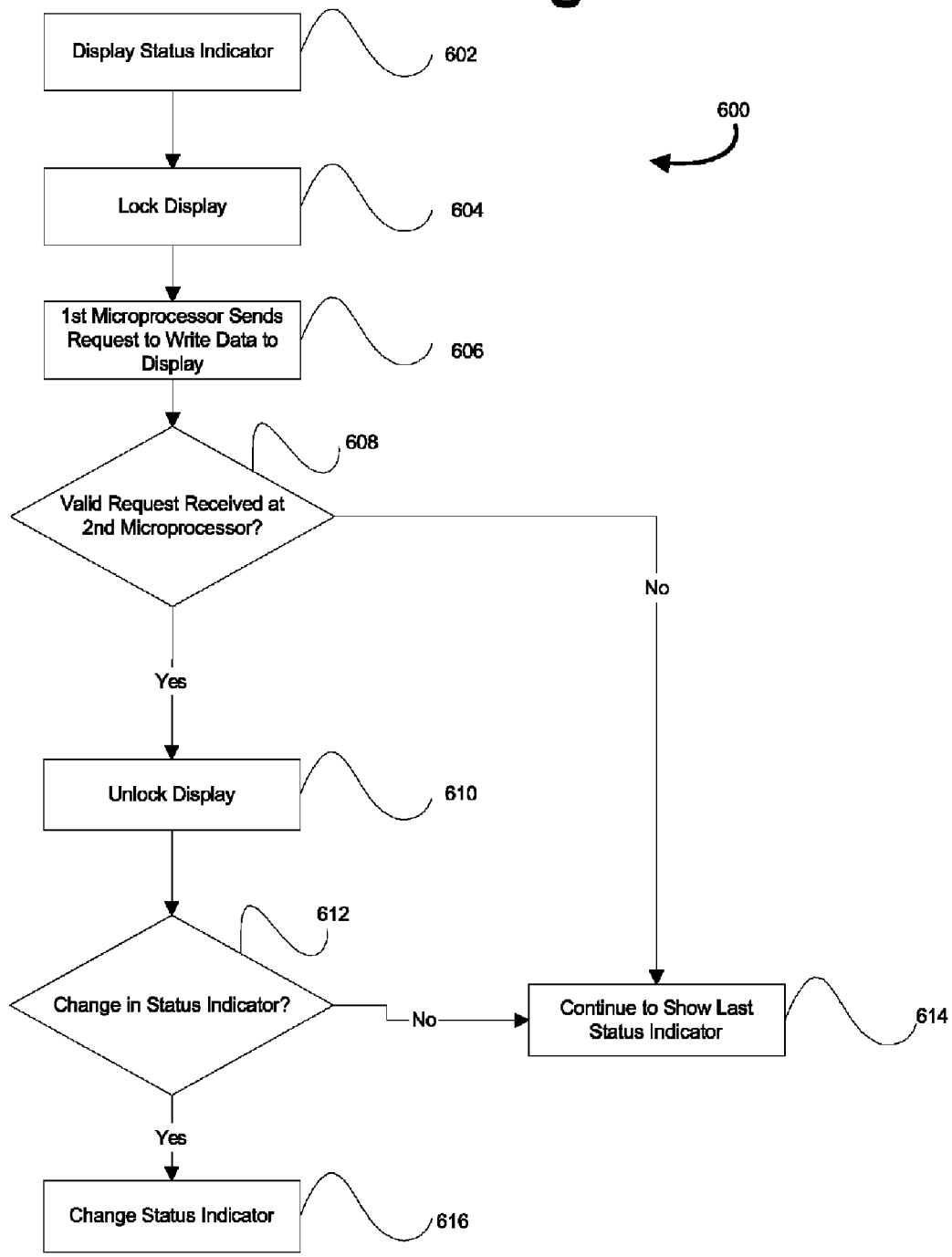

MEDICAL DEVICES USING BISTABLE DISPLAYS

Medical devices such as glucose meters and insulin pumps can use an electronic display as part of a user interface. The display can be used to indicate a status of the medical device to the patient, clinician, or physician. Examples of status indicators that can be illustrated on the display include a warning message in conjunction with an audible alarm, or a time and volume of the last medicament delivery. Under certain circumstances such as a discharged battery or a hardware failure, the display can become unreadable, which can prevent a user from being notified of a status change and, in turn, prevent a response.

In many cases, a display can consume substantial amounts of power when it is showing information. For medical devices that use a battery as a power source, a replace battery message can be shown on the display when the power is low. However, maintaining a replace battery message can, in itself, consume battery power and further decrease the battery life. The problem with showing the battery message can be more problematic when using high power emissive display technology such as an organic light emitting diode (OLED).

BRIEF DESCRIPTION OF THE DRAWINGS

FIG. 6 is a flow chart illustrating an alternative method of locking/unlocking a display to reduce the likelihood of showing an unreadable status indicator.

DETAILED DESCRIPTION OF THE DRAWINGS

Applicant believes that there is a need to integrate a display that consumes relatively small amounts of power and that can notify a user of a status of the medical device even when the battery has been discharged. In an embodiment, a medical device can include a bistable display that does not consume power unless there is a change in the output of the display. A bistable display can retain an image without using any power or driving electronics. Power is required when the when new information is written to the bistable display. An example of materials used in bistable displays include nematic crystals, polymer stabilized cholesteric liquid crystals, and electrophoretic inks E-Ink Corporation of Cambridge, Mass. has demonstrated bistable displays that maintain a readable image for over a year after being disconnected from any power and driving electronics. Bistable displays suitable for use with medical devices can include U.S. Pat. Nos. 6,531,997; 7,394,509; 7,335,405; and 7,351,506, which are hereby fully incorporated by reference herein. Before describing a medical device that integrates bistable display technology, the following will first generally describe an insulin pump.

Figure 1:
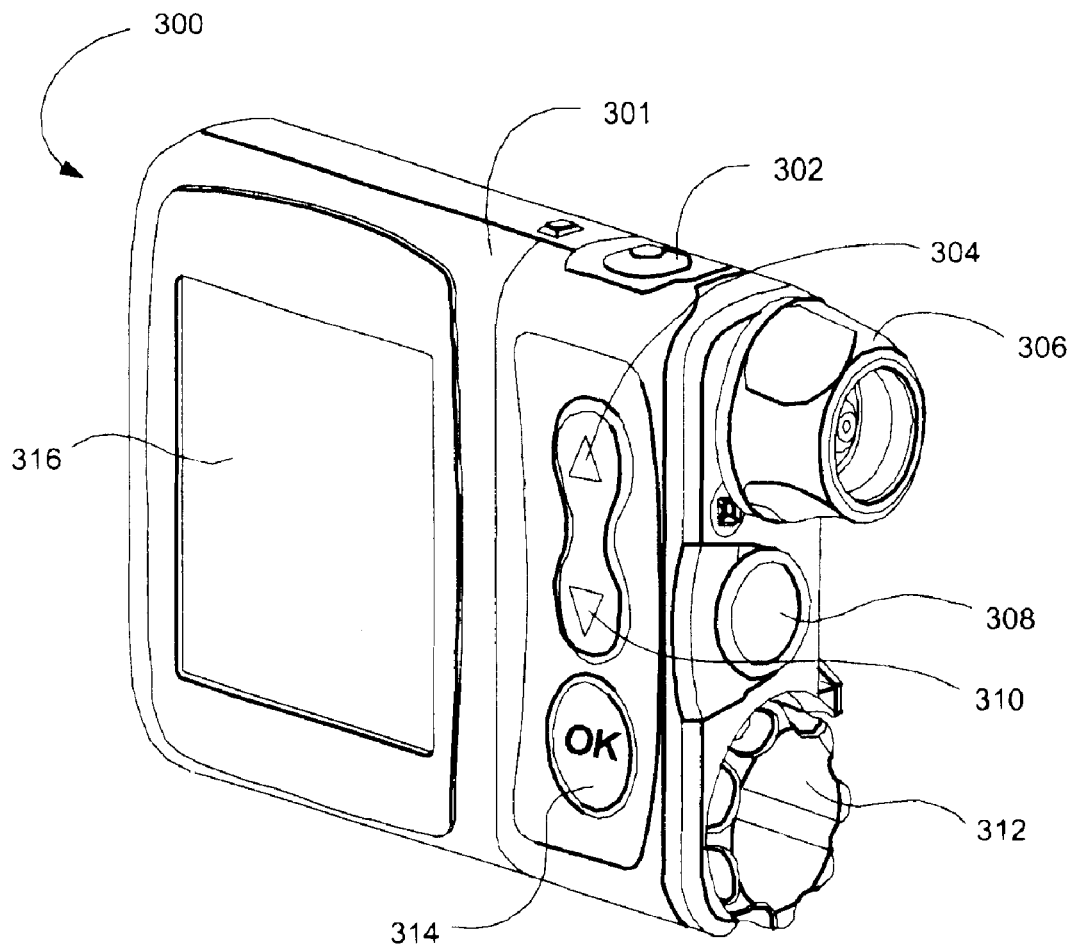
FIG. 1 is a perspective view of a pump.

FIG. 1 is a perspective view of a pump 300 that includes a housing 301, a backlight button 302, an up button 304, a cartridge cap 306, a bolus button 308, a down button 310, a battery cap 312, an OK button 314, and a display 316. Pump 300 can be configured to dispense medication such as, for example, insulin for regulating glucose levels. Pump 300 can be similar to a commercially available pump from Animas, Corp. (West Chester, Pa., Catalog No. IR 1200).

Figure 2:
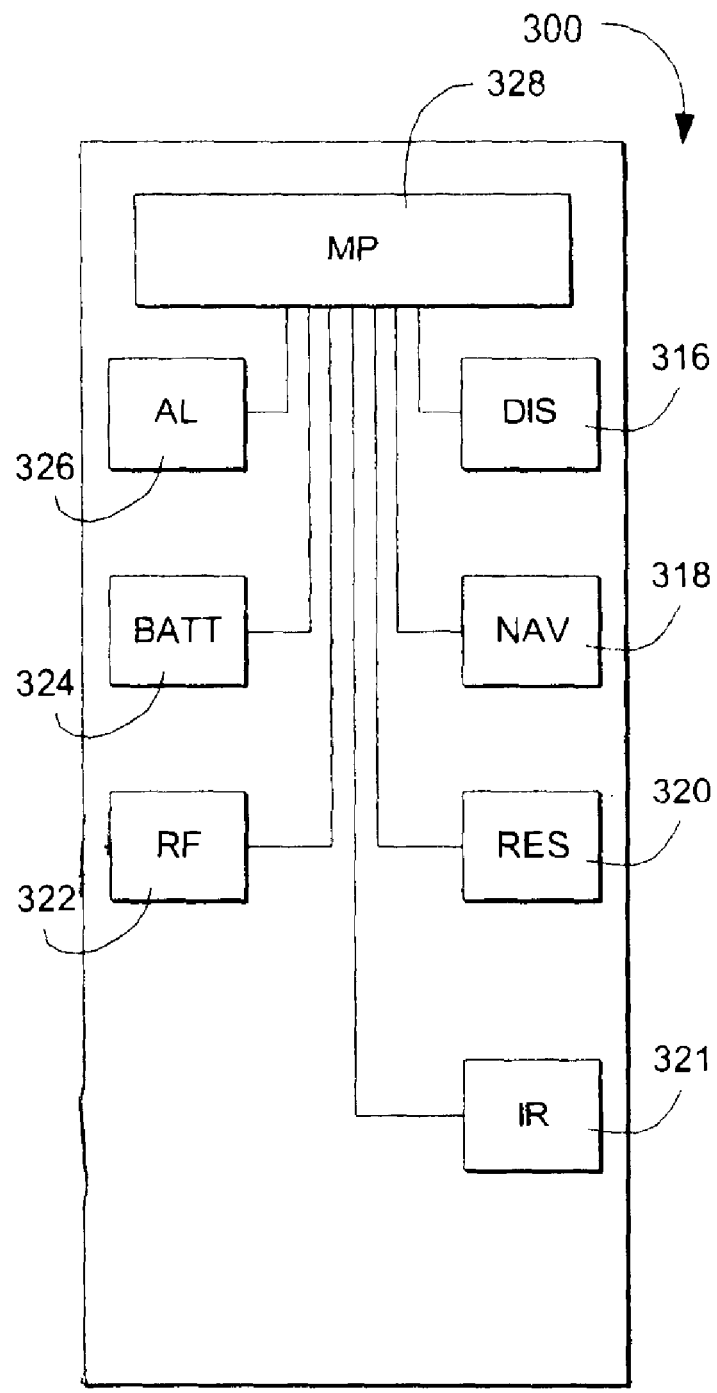
FIG. 2 is a schematic view of the functional components of the pump.

FIG. 2 is a schematic functional view of pump 300 that includes the following functional components, which are a display (DIS) 316, navigational buttons (NAV) 318, a reservoir (RES) 320, an infrared communication port (IR) 321, a radio frequency module (RF) 322, a battery (BAT) 324, an alarm (AL) 326, and a microprocessor (MP) 328. Pump 300 can also include a watchdog timer that can be a discrete electronic component or alternatively can be integrated with microprocessor 328. Although only one microprocessor 328 is shown in FIG. 2, one skilled in the art could use more than one microprocessor in pump 300. For example, a first microprocessor could be configured to control data written to display 316 and a second microprocessor could be configured to control whether power should be supplied to display 316.

Pump 300 can include mechanical or electrical components for moving fluid from reservoir 320 through a conduit that leads to the subcutaneous layer of a user. Examples of mechanical or electrical components for moving a fluid from reservoir 320 can be found in U.S. Pat. Nos. 5,041,107; 6,656,148; 7,193,521; U.S. Pre-Grant Publications No's 2008/0167618; 2005/0177108; and International Publication WO2005/113419, which are hereby fully incorporated by reference herein.

Display 316 can be controlled by microprocessor 328 and other electronic circuitry such as voltage regulators, charge pumps, biasing networks, and integrated logic. A hardware error in any part of the circuitry can cause a partial or complete loss of readability of display 316. In another embodiment, pump 300 could include two displays where one is a bistable display and the other is a non-bistable display. Some bistable displays can be relatively thin and flexible allowing the bistable display to wrap around or shape conform to the non-bistable display.

A portion of display 316 can be used to illustrate a status indicator. The status indicator can provide a user important information about a current operation of pump 300, prompt a user to provide an input to pump 300, or to change a setting of pump 300. In an embodiment, the status indicators such can be used to describe a hardware error or an alarm/warning message. Examples of hardware errors can include a communication error, motor stall error, motor encoder error, delivery timeout error, force error, power supply error and a defective or corrupted memory error. The alarm/warning messages can include replace battery, replace insulin cartridge, remove occlusion in the pump tubing or needle, a timed bolus reminder, a timed check-blood-glucose reminder, pump not primed, no cartridge is detected, insulin level too low in the cartridge, insulin amount exceeds total daily limit, insulin amount exceeds maximum bolus limit, wireless communication lost during remote bolus, insulin amount exceeds two hour limit, insulin amount exceeds maximum basal limit, basal pumping suspended, bolus canceled at pump, low battery, and low cartridge.

Figure 3:
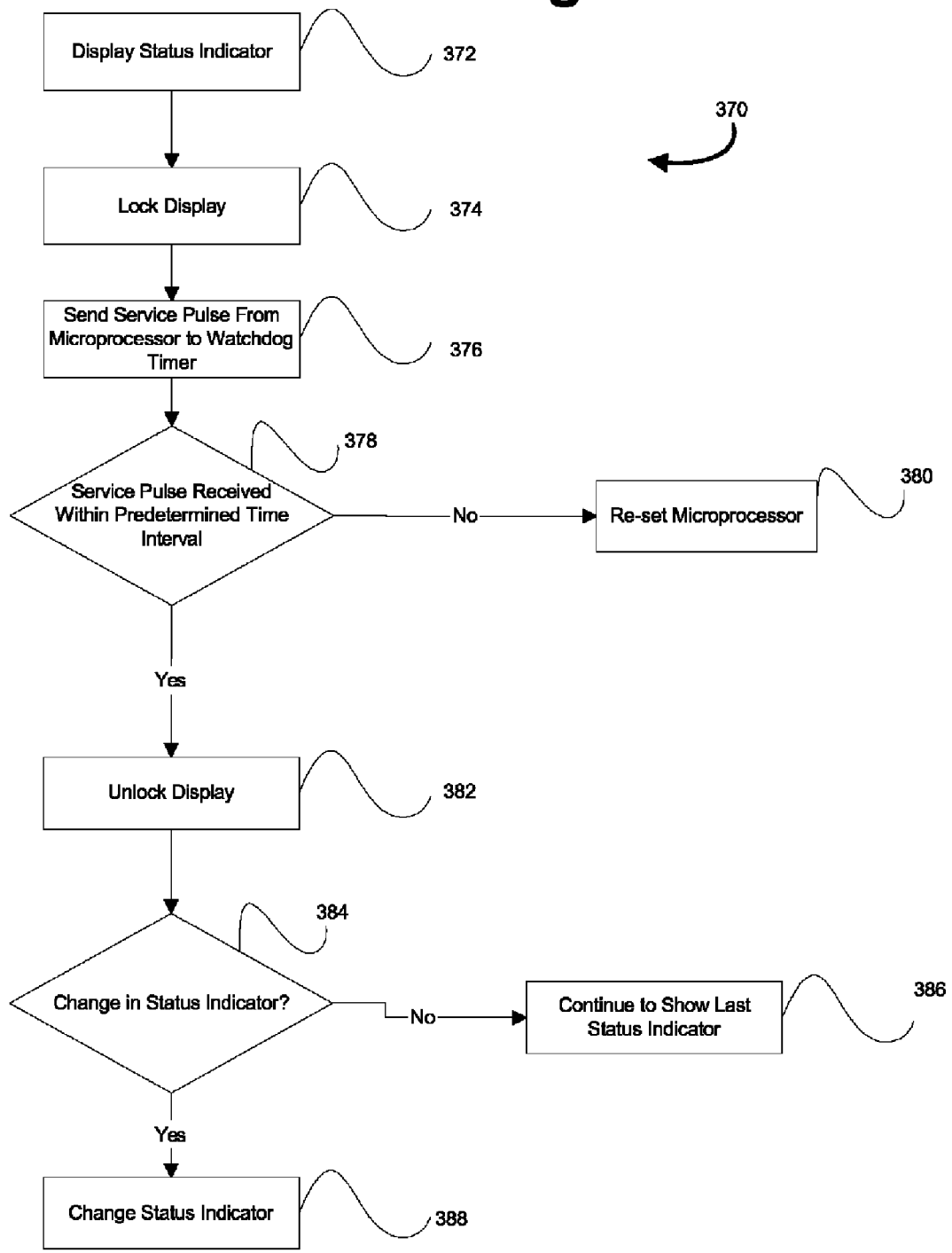
FIG. 3 is a flow chart illustrating a method of showing a status indicator that reduces the likelihood of an unreadable status indicator even if there is a discharged battery or hardware failure.

FIG. 3 illustrates a method 370 of showing a status indicator on a bistable display that reduces the likelihood of an unreadable status indicator being shown due to a discharged battery or hardware failure. Method 370 includes showing a status indicator on a display, as shown in a step 372. Next, the display is locked so that the status indicator on the screen cannot be changed, as shown in a step 374. When locked, the status indicator remains readable on the screen without using power.

In order to change the status indicator, the display must be unlocked. In an embodiment, a watchdog timer can be used to unlock the display. The microprocessor can be configured to send a service pulse to the watchdog timer at a predetermined interval, as shown in a step 376. In turn, the watchdog timer can be configured to determine whether the service pulse was received at the predetermined interval, as shown in a step 378. If the service pulse was received at the predetermined interval, then the display is unlocked, as shown in a step 382. If the service pulse was not received at the predetermined interval, then the display remains locked and the microprocessor is re-set, as shown in a step 380. The service pulse can include a signal format such as, for example, data keys, timed pulse sequences, combinatorial logic, and signal selection.

Once the display is unlocked, a step 384 can be performed by the microprocessor to determine whether a change in the status indicator has occurred since step 374. If no change in status indicator has occurred, then the display will continue to show the last status indicator, as shown in a step 386. The last status indicator can be the status indicator at the time the display was locked. If a change in status indicator has occurred, then the display will change to show a most recent status indicator, as shown in a step 386. Method 370 reduces the likelihood of showing an unreadable status indicator because of a hardware failure and/or a discharged battery. Note that a hardware failure or a discharged battery will likely prevent the microprocessor from sending a service pulse to the watchdog timer at the predetermined interval to unlock the display. Thus, if the display cannot be unlocked, then the status indicator cannot be changed. Note that even though a bistable display will reduce the amount of required power, it is still possible for a hardware error or a substantially discharged battery to cause an unintelligible message to be shown and then remain on the bistable display in the unintelligible state. The use of method 370 will increase the likelihood that once a hardware failure or discharged battery occurs, the most recent status indicator will be continually displayed, which will allow a user to more effectively troubleshoot the pump at a later time.

Although a watchdog timer is used herein to describe an unlocking/locking method, one skilled in the art could apply other types of hardware components or software algorithms to perform a system check before allowing a re-write to be made to the display. The following will describe an alternative embodiment that does not use a watchdog timer for unlocking/locking a display. FIG. 6 illustrates an alternative method 600 of showing a status indicator on a bistable display that reduces the likelihood of an unreadable status indicator being shown. Method 600 includes showing a status indicator on a display, as shown in a step 602. Next, the display is locked so that the status indicator on the screen cannot be changed, as shown in a step 604. When locked, the status indicator remains readable on the screen without using power.

In order to change the status indicator, the display must be unlocked. In an embodiment, a first microprocessor can control data written to the display and a second microprocessor can control whether power to the display should be activated. The first microprocessor can be configured to send a request to write data to the display, as shown in a step 606. In turn, the second microprocessor can be configured to determine whether the received request was a valid request, as shown in a step 608. If the received request was a valid request, then the second microprocessor activates the power supply to unlock the display, as shown in a step 610. If the received request was not a valid request, then the second microprocessor does not activate the power supply to unlock the display and will continue to show the last status indicator, as shown in a step 614.

Once the display is unlocked, a step 612 can be performed to determine whether a change in the status indicator has occurred since step 604. If no change in status indicator has occurred, then the display will continue to show the last status indicator, as shown in step 610. If a change in status indicator has occurred, then the display will change to show a most recent status indicator, as shown in a step 616. Similar to method 300, method 600 also reduces the likelihood of showing an unreadable status indicator because of a hardware failure and/or a discharged battery. Note that a hardware failure or a discharged battery will likely prevent the first microprocessor from sending a valid request to the second microprocessor, which, in turn, would prevent the power supply from being activated. It should be noted that a logical hardware device may be used as a substitute for either the first or the second microprocessor.

Figure 4:
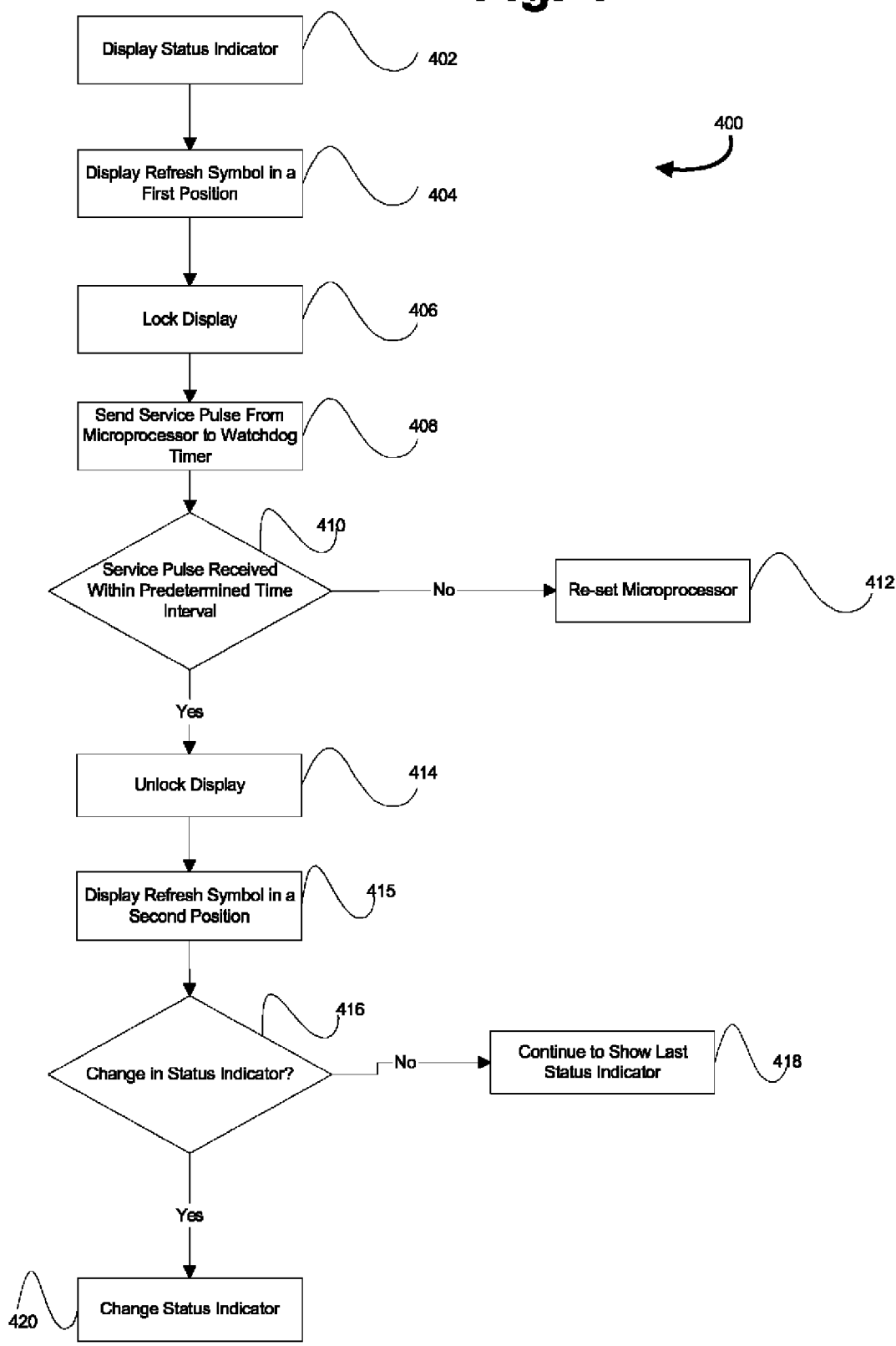
FIG. 4 is a flow chart illustrating a method of showing a status indicator and a refresh symbol that reduces the likelihood of an unreadable status indicator and also notifies a user whether the pump is operating properly.

FIG. 4 is a flow chart illustrating a method 400 for showing a status indicator and a refresh symbol. Method 400 can reduce the likelihood of showing an unreadable status indicator and also notify a user whether the pump is operating properly. The refresh symbol can periodically change, from a first position to a second position, to serve as a visual indication of proper pump operation. In an embodiment, the refresh symbol may switch from the first position to the second position during a time interval ranging from about one second to about two seconds. The time interval can be configured so that a user examining the display would be able to determine that the pump is active and working. For example, the refresh symbol could include a beating heart, a rotating pin-wheel, and a rotating clock hand. In addition, the refresh symbol could include an indication of time of day, so that the time of pump failure could be determined from the last updated time. In the event that the pump fails without warning, the refresh symbol and status indicator would remain frozen on the display indefinitely. This would provide a user with a visual indication of the failure, along with important contextual information needed to efficiently remedy the failure.

The energy required for changing the position of the refresh symbol can be relatively small when the refresh symbol is relatively small in size. The amount of energy needed to rewrite a portion of the display can be proportional to the display area used by the refresh symbol. When making a change to a portion of a bistable display, it may not be necessary to re-write the entire area of the display. It should be noted that the energy needed to update an entire bistable display is small in comparison to the energy that would be needed to update and maintain a non-bistable display.

In FIG. 4, method 400 includes showing a status indicator on a display, as shown in a step 402. In addition, a refresh symbol is also shown on the display, as shown in a step 404. Next, the display is locked so that the status indicator and the refresh symbol on the screen cannot be changed, as shown in a step 406.

In order to change the status indicator, the display must be unlocked. In an embodiment, a watchdog timer can be used to unlock the display. The microprocessor can be configured to send a service pulse to the watchdog timer at a predetermined interval, as shown in a step 408. In turn, the watchdog timer can be configured to determine whether the service pulse was received at the predetermined interval, as shown in a step 410. If the service pulse was received at the predetermined interval, then the display is unlocked, as shown in a step 414. If the service pulse was not received at the predetermined interval, then the display remains locked and the microprocessor is re-set, as shown in a step 412.

Once the display is unlocked in step 414, the display will show a refresh symbol in a second position, as shown in a step 415. The change in the refresh symbol from the first to the second position will provide a simple form of animation that allows a user to know that the pump is operating properly. Next, a step 416 can be performed by the microprocessor to determine whether a change in the status indicator has occurred since step 406. If no change in status indicator has occurred, then the display will continue to show the last status indicator, as shown in a step 418. If a change in status indicator has occurred, then the display will change to show a most recent status indicator, as shown in a step 420. In contrast to method 300, method 400 not only reduces the likelihood of showing an unreadable status indicator, but also notifies a user when the pump has stopped operating through the use of the refresh symbol.

Figure 5:
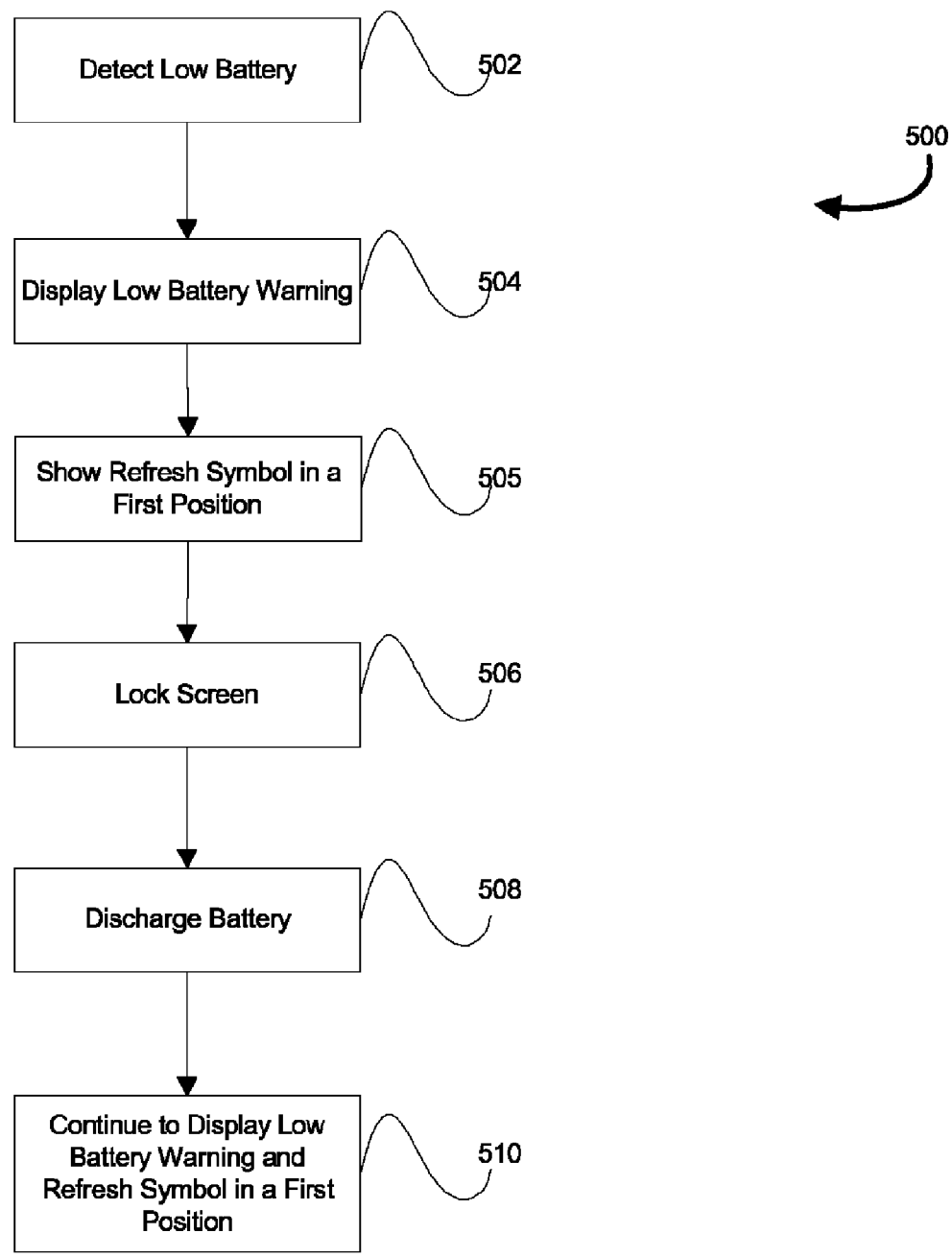
FIG. 5 is a flow chart illustrating a method of showing a low battery warning and a refresh symbol that accounts for the situation where the battery later becomes discharged.

FIG. 5 illustrates a method 500 that shows a specific status indicator, which is a low battery warning, for the situation in which the battery later becomes discharged. Method 500 includes detecting a low power level in a battery, as shown in a step 502. Once a low battery level is detected by the microprocessor, a low battery warning is shown on the display, as shown in a step 504. A refresh symbol in a first position is shown on the display, as shown in a step 505. Next, the display is locked so that the status indicator and the refresh symbol in the first position cannot be changed, as shown in a step 506.

Once the display is locked, the battery substantially discharges, as shown in a step 508. For this situation, the microprocessor cannot unlock the display because battery power is needed to send a service pulse at the appropriate time interval. Thus, the display will continue to show the low battery warning and the refresh symbol in the first position, as shown in a step 510. Even if the battery has been discharged for a relatively long period of time, a user will still be prompted by the replace battery warning on the bistable display to install a new battery. In addition, a user can quickly realize that the pump is not operating properly because the refresh symbol is frozen and not changing positions with time.

For the situation in which a non-bistable LCD display is used, power is required to show and change a status indicator. The non-bistable LCD display will become blank when the battery discharges. Thus, if the battery has been discharged, the display will not show a status indicator that prompts the user to address a particular type of problem. A user will then have to perform a more complex and time-consuming investigation to fix the pump and take appropriate actions. The delay may prevent the user from responding in a timely and optimal response to restore his or her blood glucose levels. In addition, if the pump has a blank or static display when it is operating properly, a user will not quickly realize when there is an operational problem with the pump.

What is claimed is:

1. A method of displaying an image on a medical device display, comprising:
    providing a medical infusion device having a housing, a cavity for receiving a cartridge containing a quantity of medication, a keypad for receiving user input, at least one microprocessor, a power supply, and a display unit comprising a first display and a second display, wherein at least one of the first display and second display is a bistable display,
    providing power from the power supply to the first display and second display,
    generating a message for display on the second display unit,
    displaying the message on the second display unit,
    removing power to the second display unit; and
    retaining the visibility of the message on the display screen.

2. The method of claim 1 wherein the message indicates at least one condition selected from the following: replace battery, replace insulin cartridge, remove occlusion in the pump tubing or needle, a timed bolus reminder, a timed check-blood-glucose reminder, pump not primed, no cartridge is detected, insulin level too low in the cartridge, insulin amount exceeds total daily limit, insulin amount exceeds maximum bolus limit, wireless communication lost during remote bolus, insulin amount exceeds two hour limit, insulin amount exceeds maximum basal limit, basal pumping suspended, bolus canceled at pump, low battery, and low cartridge.

* * * * *